United States Patent [19]

Nakada et al.

[11] Patent Number: 5,789,632
[45] Date of Patent: Aug. 4, 1998

[54] PROCESS OF PURIFYING 1,1,1,3,3,-PENTAFLUORO-2,3 DICHLOROPROPANE

[75] Inventors: Tatsuo Nakada; Hirokazu Aoyama, both of Osaka, Japan

[73] Assignee: Daikin Industries, Ltd., Osaka, Japan

[21] Appl. No.: 666,353

[22] PCT Filed: Dec. 21, 1994

[86] PCT No.: PCT/JP94/02161
§ 371 Date: Jun. 20, 1996
§ 102(e) Date: Jun. 20, 1996

[87] PCT Pub. No.: WO95/17366
PCT Pub. Date: Jun. 29, 1995

[30] Foreign Application Priority Data

Dec. 22, 1993 [JP] Japan ................................. 5-324710

[51] Int. Cl.$^6$ ................................. C07C 17/38; C07C 17/383
[52] U.S. Cl. ................................. 570/178; 570/177
[58] Field of Search ................................. 570/178

[56] References Cited

FOREIGN PATENT DOCUMENTS 2196734  8/1990  Japan ................................. 570/178

*Primary Examiner*—Alan L. Rotman
*Attorney, Agent, or Firm*—Birch, Stewart, Kolasch & Birch, LLP

[57] ABSTRACT

A mixture containing hydrogen fluoride and 1,1,1,3,3-pentafluoro-2,3-dichloropropane is subjected to distillation to form an azeotropic composition of 85 to 95 mol % of hydrogen fluoride and 15 to 5 mol % of 1,1,1,3,3-pentafluoro-2,3-dichloropropane, and the azeotropic composition is liquid-separated to form a lower liquid phase. Then, an azeotropic composition is withdrawn from the lower liquid phase by distillation, whereby 1,1,1,3,3-pentafluoro-2,3-dichloropropane is obtained.

Without formation of an aqueous solution of diluted hydrofluoric acid, 1,1,1,3,3-pentafluoro-2,3-dichloropropane is obtained which is substantially free of hydrogen fluoride.

8 Claims, 2 Drawing Sheets

PROCESS OF PURIFYING 1,1,1,3,3,-PENTAFLUORO-2,3 DICHLOROPROPANE

TECHNICAL FIELD

The present invention relates to a process of concentrating or purifying 1,1,1,3,3-pentafluoro-2,3-dichloropropane (hereinafter, referred to as R-225da) by separating hydrogen fluoride (hereinafter, referred to as HF) from a mixture which mainly contains HF and R-225da, and a process of concentrating or purifying HF by separating R-225da from such a mixture.

BACKGROUND ART

R-225da is usually produced by reacting a chlorinated hydrocarbon such as hexachloropropene with HF under the presence of for example antimony halide as catalyst. As a separation manner of R-225da from a reaction mixture from the reaction step, a process is employed in which the reaction mixture is subjected to simple distillation so that the catalyst is removed and a resulted mixture comprising HF and R-225da is washed with water so as to isolate R-225da. However, such a separation manner forms a large amount of an aqueous solution of diluted hydrofluoric acid, and an apparatus is therefore required which treats the solution. Further, a large amount of an alkali is required which neutralizes the solution. Thus, the above described separation manner is not necessarily effective.

DISCLOSURE OF INVENTION

The present inventors have made extensive studies on a process which separates HF from a mixture comprising HF (of which boiling point is 20° C. at 1 atm.) and R-225da (of which boiling point is 50.4° C. at 1 atm.) as main components, and found that HF and R-225da form a minimum azeotropic composition having a molar ratio of about 90/10 (its boiling point is 18° C. under a pressure of 1 Kg/cm²-abs).

It has been further found that such an azeotropic composition is separated into an upper liquid phase (liquid layer) which is rich in HF and a lower liquid phase which is rich in R-225da (liquid layer) (namely, liquid separation) at a temperature which is generally used in industries, for example in a range of 80° to −60° C., which have resulted in the present invention.

Especially, the present invention provides an azeotropic composition (or an azeotropic mixture) which consists substantially of HF and R-225da, and in particular an azeotropic composition which contains 85 to 95 mol % of HF and 15 to 5 mol % of R-225da (boiling point in a range of 18° to 50° C.) under a pressure in a range of 1 to 5 Kg/cm² (abs).

In addition, the present invention provides a process of separating HF or R-225da from a mixture which comprises HF and R-225da characterized in that the mixture is subjected to distillation using the formation of the azeotropic composition so that HF and R-225da is distilled off as the azeotropic composition, and the balance are obtained as a bottom product. The balance is rich in one of the components, and preferably consists substantially of one component.

That is, the present invention provides a process of concentrating (or purifying) R-225da or HF by separating HF or R-225da from a mixture comprising HF and R-225da as a feed in which process the mixture is subjected to an azeotropic distillation step so as to distill off an azeotropic composition from an enriching zone of the distillation step, for example from a top of a distillation column, and obtain, from a recovery zone of the distillation step, for example a bottom of the distillation column, R-225da of which HF content is reduced relative to that of the feed and which is preferably substantially free of HF, or HF of which R-225da content is reduced relative to that of the feed and which is preferably substantially free of R-225da, depending on a composition of the mixture.

Further, the present invention provides a process of concentrating R-225da by separating HF which process is characterized in that an azeotropic mixture resulted from azeotropic distillation which consists substantially of HF and R-225da is phase separated into an upper liquid phase which is rich in HF and a lower liquid phase which is rich in R-225da, and the lower liquid phase is supplied to another distillation column so that an azeotropic composition is again distilled off from its top and R-225da which does not substantially contain HF is obtained from its bottom. The present invention also provides a process for concentrating HF by separating R-225da in which process a separated upper liquid phase is subjected to azeotropic distillation so as to distill off an azeotropic composition from a column top and HF which is substantially free from R-225da is obtained from a column bottom.

In the context of the present specification, "depending on a composition of the mixture" is intended to mean that which of HF and R-225da is obtained from the recovery zone is necessarily determined based on a result when HF and R-225da compositions of the mixture as the feed are compared with the those compositions of the azeotropic mixture.

That is, it means that when an amount of HF contained in the feed is less than an amount which is required for the formation of the azeotropic composition with R-225da contained in the feed, a mixture is obtained from the recovery zone of the distillation step such as a column bottom of which HF content is smaller than an HF content of the feed and of which main component is R-225da, and preferably R-225da which is substantially free of HF is obtained from the recovery zone. It also means that to the contrary when an amount of HF contained in the feed is larger than an amount which is required for the formation of the azeotropic composition with R-225da contained in the feed, a mixture is obtained from the recovery zone of the distillation step such as a column bottom of which R-225da content is smaller than an R-225da content of the feed and of which main component is HF, and preferably HF which is substantially free of R-225da is obtained from the recovery zone.

DETAILED DESCRIPTION OF INVENTION

Figure 1:
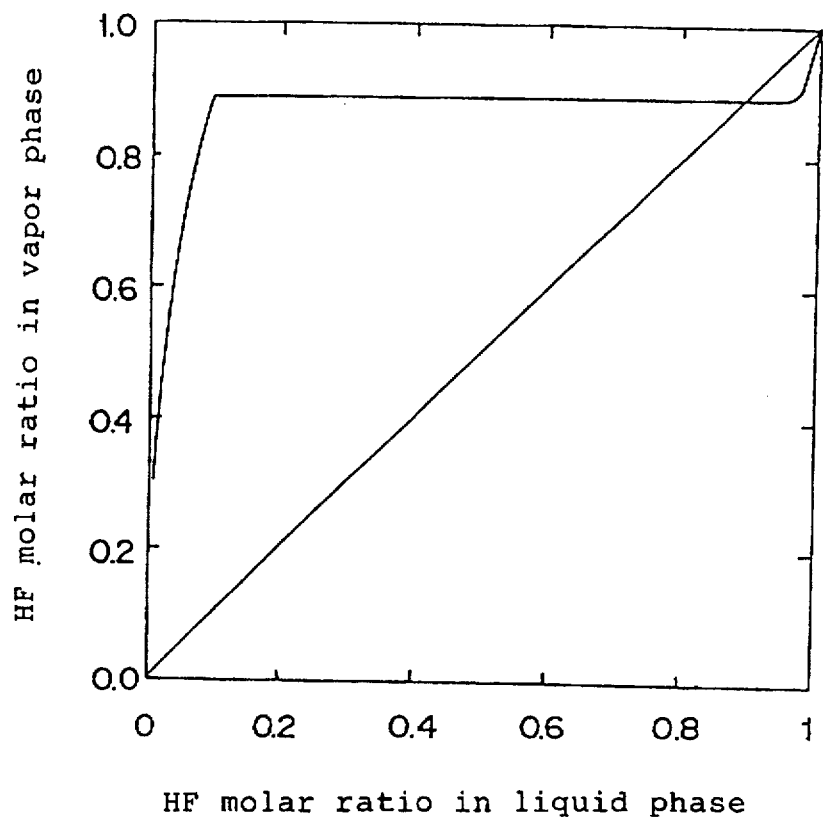
FIG. 1 is a graph showing a vapor-liquid equilibrium of a binary system of HF-R-225da.

According to the present invention, the distillation of the mixture consisting substantially of HF and R-225da distills off the azeotropic mixture of R-225da and HF from the column top, and the mixture as a bottom product is obtained from the column bottom. A content of either one component of the mixture is substantially increased relative to a content of that component in the feed (thus, a content of the other component is substantially reduced), and preferably the mixture hardly contains the other component.

The mixture of HF and R-225da which is supplied to the azeotropic distillation as the feed may have any composition. Usually, the content of R-225da of the mixture is not more than 10 mol %, and preferably not more than 5 mol %.

The mixture as the feed may be of two separated liquid phase condition, in which case it may be supplied to the distillation step as it is or after mixing using any suitable means so as to homogenize, or only the upper phase or the lower phase may be supplied to the distillation step. Alternatively, each phase may be supplied to a different distillation step.

It is noted that the distilled azeotropic composition is liquid-separated into the upper phase which is rich in HF and the lower phase which is rich in R-225da, and these two phases may be again supplied to the distillation steps; namely, the lower phase which is rich in R-225da is subjected to the distillation so as to distill off the azeotropic composition of HF and R-225da, whereby R-225da which is substantially free of HF may be obtained as a bottom product, and the upper phase may be similarly distilled so as to obtain HF which is substantially free of R-225da as a bottom product.

Accordingly, in one preferable embodiment of the present invention, a mixture which contains HF and R-225da is subjected to the distillation so that an azeotropic composition is distilled off which contains 85 to 95 mol % of HF and 15 to 5 mol % of R-225da; the azeotropic composition is liquid separated so that the lower phase which is rich in HF and the upper phase which is rich in R-225da are formed; and then the lower liquid phase is subjected to a distillation step again so as to remove the azeotropic composition of HF and R-225da from the lower phase, whereby R-225da which is substantially free of HF is obtained as a bottom product.

In the present invention, the mixture as the feed may contain, in addition to HF and R-225da, an additional component(s) unless it substantially provides the azeotropic phenomenon with an adverse effect. For example, the mixture may contain a material of which boiling point is higher than those of HF and R-225da (for example, catalyst which is required for the production of R-225da), or the mixture may be a reaction product which contains unreacted raw material(s) which is required for the production of R-225da. The catalyst is, for example, antimony halide. As the reaction raw materials, hexachloropropene and 3,3,3-trifluoro-1,2,2-trichloropropene can be exemplified. Such a reaction product contains, for example, 94 mol % of HF and 5 mol % of R-225da, and it contains, in addition to those, 0.5 mol % of the antimony halide and 0.5 mol % of 3,3,3-trifluoro-1,2,2-trichloropropene.

As to a temperature at which the azeotropic composition is subjected to the liquid separation, a lower temperature is better since the lower temperature leads to an increased ratio of R-225da contained in the lower phase and an increased ratio of HF contained in the upper phase. Since the azeotropic composition according to the present invention is liquid-separated in a wide temperature range, the liquid separation can be carried out at any temperature provided that such a temperature is industrially possible. Thus, the liquid-separation temperature is not limited. However, the liquid separation temperature is preferably in a range of 80° to −60° C., and more preferably in a range of 40 to −40 ° C. Considering energy which is required for cooling, the liquid separation is most preferably carried out at a temperature in a range of 20° to −20° C. The liquid separation can be easily carried out by settling in a normal vessel the mixture which is to be separated. Coalescer may be provided in the vessel so as to promote the liquid separation.

In the present invention, HF and R-225da form the azeotropic composition at any pressure if it is an industrially applicable pressure. For example, an azeotropic composition (85 mol % of HF and 15 mol % of R-225da, boiling point of 42° C. at a pressure of 3.1 Kg/cm$^2$-abs) and an azeotropic composition (87 mol % of HF and 13 mol % of R-225da, boiling point of 18 ° C at a pressure of 1 Kg/cm$^2$-abs) are formed.

A distillation apparatus which is used for the azeotropic distillation according to the present invention may be any apparatus which has functions necessary for the distillation. A simple distillation apparatus or a fractionation apparatus having trays or packing may be used. The latter is in particular preferable. The distillation may be carried out batch-wise or continuously.

For example, the concentrated or purified hydrogen fluoride obtained by the distillation may be re-used for the reaction for the production of R-225da. The azeotropic composition of HF and R-225da can be used as a reflux stream which is returned to the distillation step as it is, or it can be used for the next distillation after the liquid separation thereof. R-225da obtained from the column bottom of the distillation step can be used as it is as a final product or it may be subjected to an additional treatment, for example a distillation so as to remove a trace amount of impurities.

EXAMPLES

The present invention will be explained hereinafter with reference to Examples:

Example 1

A vapor-liquid equilibrium of R-225da and HF was measured at a temperature of 40° C. under a pressure of 3.1 atm (abs). Upon the measurement of the vapor-liquid equilibrium, R-225da and HF were mixed at a predetermined ratio and kept them at 40° C., of which vapor phase was analyzed. A gas chromatography (GLC) equipped with a TCD detector was used for the purpose of R-225da measurement, and an F-ion meter was used for the purpose of F ion concentration measurement after neutralization of HF. The measurement results are shown in FIG. 1.

It has been found based on FIG. 1 that HF and R-225da form the azeotropic composition (a ratio of HF:R-225da was about 9 mol:1 mol). The boiling point was 42° C. Thus, it has been confirmed that HF (of which boiling point is 65° C. at 3.1 atm) and R-225da (of which boiling point is 110° C. at 3.1 atm) form the minimum azeotropic composition.

Similarly to the above, other vapor-liquid equilibriums were also measured under different pressures, the results thereof are as those described in the above with respect to the azeotropic composition.

Example 2

A mutual solubility between HF and R-225da was measured. For this measurement, a manner was employed in which R-225da and HF mixed in a predetermined ratio were gradually cooled and a temperature was detected at which the mixture was separated into two phases.

Figure 2:
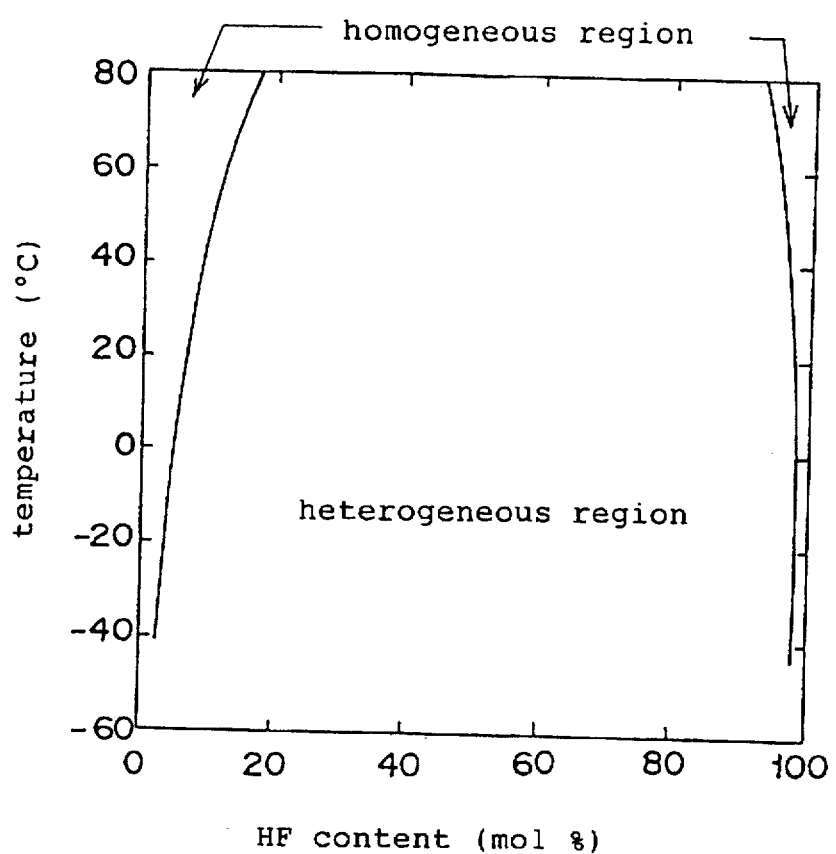
FIG. 2 is a graph showing a mutual solubility (a liquid-liquid equilibrium) of a binary system of HF-R-225da.

The measurement results are shown in FIG. 2 in which mol % of HF is plotted along the abscissa axis and temperature is plotted along the ordinate axis. Liquid of which composition is within the center region of three regions in the graph which are divided by the solid lines cannot be substantially present as a single homogeneous phase liquid and such liquid is phase-separated into homogeneous liquid of which composition is within the right side region and homogeneous liquid of which composition is within the left side region.

Since an HF concentration in the azeotropic composition of HF and R-225da is about 10 to 15 mol %, it is seen from FIG. 2 that the azeotropic composition is separated into two liquid phases at any industrially possible temperature, for example in a range of 80° to −60° C., and preferably in a range of 40° to −40° C.

Example 3

After sufficiently degassing a stainless steel made distillation apparatus (packing height: 50 cm, theoretical plate number: 20 stages, column diameter: 25 mm), a mixture of 800 g of HF (40 mol) and 200 g of R-225da (1 mol) was charged into a bottom (still pot) of the column, and the apparatus was operated at a total reflux condition (operating pressure: 3.1 Kg/cm²-abs). When gas from the column top was analyzed, a ratio of HF:R-225da in the gas was found about 9 mol:1 mol (column top temperature was 42° C.). While operating at the total reflux condition, distillates were intermittently removed from the distillation system to the outside. During the intermittent removal, the ratio of HF to R-225da of the distillate was substantially not changed until almost all R-225da was distilled off from the apparatus. A content of R-225da in the obtained bottom product was 13 mol %.

In this way, 357 g of the azeotropic composition was obtained. The azeotropic composition was separated into two phases at a temperature of 30° C. The composition was further cooled to 0° C., and then the lower liquid phase which was rich in R-225da was withdrawn to obtain a mixture (145 g) of HF and R-225da (HF: 5 mol).

This lower phase was again distilled. 3 Grams of the azeotropic composition was distilled off from the column top and 141 g of R-225da which did not substantially contain HF (HF content is not more than 0.05 mol %) was obtained from the column bottom.

Example 4

Operating similarly to Example 3, 357 g of the distilled azeotropic composition was obtained. The azeotropic composition was liquid separated while keeping it at a temperature of 20° C., and then the lower phase which was rich in R-225da was withdrawn to obtain 129 g of a mixture of R-225da and HF (HF content: 7.5 %).

The lower phase was again distilled and 5 g of the azeotropic composition was removed as the first distillate and 123 g of R-255da was obtained which did not substantially contain HF.

We claim:

1. An azeotropic composition consisting of 85 to 95 mol% of hydrogen fluoride and 15 to 5 mol% of 1,1,1,3,3-pentafluoro-2,3-dichloropropane.

2. An azeotropic composition consisting substantially of 85 to 95 mol% of hydrogen fluoride and 15 to 5 mol% of 1,1,1,3,3-pentafluoro-2,3-dichloropropane having a boiling point in a range of 16 to 19° C. at a pressure of 1 Kg/cm²-abs.

3. A process of separating hydrogen fluoride or 1,1,1,3,3-pentafluoro-2,3-dichloropropane from a mixture which comprises hydrogen fluoride and 1,1,1,3,3-pentafluoro-2,3-dichloropropane wherein the mixture is subjected to distillation so that hydrogen fluoride and 1,1,1,3,3-pentafluoro-2,3-dichloropropane are distilled off as an azeotropic composition thereof.

4. A process of purifying 1,1,1,3,3-pentafluoro-2,3-dichloropropane characterized in that an azeotropic composition containing hydrogen fluoride and 1,1,1,3,3-pentafluoro-2,3-dichloropropane is liquid-separated to obtain a lower liquid phase which is rich in 1,1,1,3,3-pentafluoro-2,3-dichloropropane, which phase is subjected to a distillation step so that an azeotropic composition of hydrogen fluoride and 1,1,1,3,3-pentafluoro-2,3-dichloropropane is withdrawn from the lower liquid phase, whereby 1,1,1,3,3-pentafluoro-2,3-dichloropropane is obtained which is substantially free of hydrogen fluoride.

5. The process of claim 3, wherein the azeotropic composition consists essentially of 85 to 95 mol% of hydrogen fluoride and 15 to 5 mol% of 1,1,1,3,3-pentafluoro-2,3-dichloropropane.

6. The process of claim 4 wherein the azeotropic composition consists essentially of 85 to 95 mol% of hydrogen fluoride and 15 to 5 mol% of 1,1,1,3,3-pentafluoro-2,3-dichloropropane.

7. The process of claim 5, wherein the azeotropic composition has a boiling point in a range of 16 to 19° C. at a pressure of Kg/cm²-abs.

8. The process of claim 5, wherein the azeotropic composition has a boiling point in a range of 16 to 19° C. at a pressure of Kg/cm² -abs.

* * * * *

UNITED STATES PATENT AND TRADEMARK OFFICE
CERTIFICATE OF CORRECTION

PATENT NO. : 5,789,632
DATED : August 4, 1998
INVENTOR(S) : Tatsuo NAKADA et al.

It is certified that error appears in the above-identified patent and that said Letters Patent is hereby corrected as shown below:

On the title page and Column 1, Line 1 and 2,

Correcting the title of Section "[54]"     change "1,1,1,3,3,-PENTAFLUORO-2,3 DICHLOROPROPANE" to --1,1,1,3,3-PENTAFLUORO-2,3-DICHLOROPROPANE--.

Signed and Sealed this

Eleventh Day of May, 1999

Attest:

Q. TODD DICKINSON

Attesting Officer     Acting Commissioner of Patents and Trademarks